(12) United States Patent
Minfelde et al.

(10) Patent No.: US 10,987,141 B2
(45) Date of Patent: Apr. 27, 2021

(54) VERTEBRAL IMPLANT, METHOD FOR THE PLACEMENT OF SUCH AN IMPLANT AND TOOL FOR THE PLACEMENT OF THE IMPLANT

(71) Applicants: BPATH, Paris (FR); Jacques Senegas, Talence (FR)

(72) Inventors: Richard Laurent Minfelde, Paris (FR); Jacques Senegas, Talence (FR)

(73) Assignees: BPATH, Paris (FR); Jacques Senegas, Talence (FR)

( * ) Notice: Subject to any disclaimer, the term of this patent is extended or adjusted under 35 U.S.C. 154(b) by 0 days.

(21) Appl. No.: 15/755,980

(22) PCT Filed: Aug. 2, 2016

(86) PCT No.: PCT/EP2016/068472
§ 371 (c)(1),
(2) Date: Feb. 27, 2018

(87) PCT Pub. No.: WO2017/036709
PCT Pub. Date: Mar. 9, 2017

(65) Prior Publication Data
US 2019/0038323 A1 Feb. 7, 2019

(30) Foreign Application Priority Data
Aug. 31, 2015 (FR) ...................................... 1558077

(51) Int. Cl.
*A61B 17/70* (2006.01)
*A61B 17/17* (2006.01)
(Continued)

(52) U.S. Cl.
CPC ...... *A61B 17/7064* (2013.01); *A61B 17/1757* (2013.01); *A61B 17/282* (2013.01);
(Continued)

(58) Field of Classification Search
CPC ... A61B 17/7064; A61B 17/28; A61B 17/808; A61F 2/4455
See application file for complete search history.

(56) References Cited

U.S. PATENT DOCUMENTS 5,395,370 A * 3/1995 Muller ............... A61B 17/7005
294/101
6,238,396 B1 * 5/2001 Lombardo ......... A61B 17/7052
606/251

(Continued)

FOREIGN PATENT DOCUMENTS

WO WO 2010/019783 A2 2/2010

OTHER PUBLICATIONS

Amit Agarwala et al., "Do facet screws provide the required stability in lumbar fixation?A biomechanical comparison of the Boucher technique and pedicular fixation in primary and circumferential fusions", Clinical Biomechanics 27 (2012) pp. 64-70.
(Continued)

*Primary Examiner* — Ellen C Hammond
*Assistant Examiner* — Tara Rose E Carter
(74) *Attorney, Agent, or Firm* — Muncy, Geissler, Olds & Lowe, P.C.

(57) ABSTRACT

The invention relates to a vertebral implant placed after a laminectomy and fixed by transfacet screws arranged in a translaminar direction. The invention also relates to a placement instrument and to a method for the placement of an implant.

12 Claims, 6 Drawing Sheets

(51) Int. Cl.
    A61B 17/28    (2006.01)
    A61B 17/80    (2006.01)
    A61B 17/86    (2006.01)
    A61F 2/44     (2006.01)
    A61F 2/46     (2006.01)
    A61B 17/56    (2006.01)
    A61F 2/30     (2006.01)

(52) U.S. Cl.
    CPC ...... *A61B 17/2816* (2013.01); *A61B 17/7052* (2013.01); *A61B 17/7058* (2013.01); *A61B 17/7059* (2013.01); *A61B 17/808* (2013.01); *A61B 17/8042* (2013.01); *A61B 17/863* (2013.01); *A61B 17/8605* (2013.01); *A61F 2/4405* (2013.01); *A61F 2/4611* (2013.01); *A61B 2017/564* (2013.01); *A61F 2002/30471* (2013.01); *A61F 2002/30622* (2013.01); *A61F 2002/30649* (2013.01)

(56)  References Cited

U.S. PATENT DOCUMENTS

| | | | | |
|---|---|---|---|---|
| 6,669,697 | B1* | 12/2003 | Pisharodi | A61B 17/7007 606/250 |
| 6,669,698 | B1* | 12/2003 | Tromanhauser | A61B 17/1615 606/104 |
| 7,766,943 | B1* | 8/2010 | Fallin | A61B 17/7085 606/264 |
| 7,955,358 | B2* | 6/2011 | Albert | A61B 17/7034 606/266 |
| 8,080,045 | B2* | 12/2011 | Wotton, III | A61B 17/8866 606/324 |
| 2003/0040746 | A1* | 2/2003 | Mitchell | A61B 17/1606 623/17.11 |
| 2004/0230201 | A1 | 11/2004 | Yuan et al. | |
| 2006/0241771 | A1 | 10/2006 | Gordon et al. | |
| 2008/0234739 | A1* | 9/2008 | Hudgins | A61B 17/7023 606/255 |
| 2009/0012571 | A1* | 1/2009 | Perrow | A61B 17/1671 606/280 |
| 2009/0018586 | A1 | 1/2009 | Butler et al. | |
| 2009/0043339 | A1 | 2/2009 | Tepper et al. | |
| 2009/0216273 | A1 | 8/2009 | Cox | |
| 2011/0046675 | A1 | 2/2011 | Barrus et al. | |
| 2011/0319925 | A1 | 12/2011 | Helgerson | |
| 2012/0197311 | A1 | 8/2012 | Kirschman | |
| 2013/0053854 | A1* | 2/2013 | Schoenefeld | A61B 17/1757 606/87 |

OTHER PUBLICATIONS

Kingsley R. Chin, MD et al., "Stability of transforaminal lumbar interbody fusion in the setting of retained facets and posterior fixation using transfacet or standard pedicle screws" The Spine Journal 2013, pp. 1-6, Received Aug. 31, 2012; revised May 17, 2013; accepted Jun. 29, 2013.

Yuanwu Cao et al., "The combined use of unilateral pedicle screw and contralateral facet joint screw fixation in transforaminal lumbar interbody fusion", Eur Spine J (2015), 24: pp. 2607-2613, Received: Jul. 28, 2014 / Revised: Jul. 8, 2015 / Accepted: Jul. 8, 2015 / Published online: Jul. 15, 2015 Springer-Verlag Berlin Heidelberg 2015.

Yong Hu et al., "Anatomic study of the lumbar lamina for safe and effective placement of lumbar translaminar facet screws", Journal of International Medical Research, 2019, Pre-Clinical Research Report, pp. 1-12., Date received: Apr. 9, 2019; accepted: Jul. 24, 2019.

* cited by examiner

VERTEBRAL IMPLANT, METHOD FOR THE PLACEMENT OF SUCH AN IMPLANT AND TOOL FOR THE PLACEMENT OF THE IMPLANT

The present invention relates to the field of surgical implants for the spinal column, e.g. for arthrodesis of the lumbar spine. The invention relates more particularly to implants put into place by a posterior approach.

STATE OF THE ART

Arthrodesis is a type of surgery aiming to stabilize a joint in order to make that joint less painful.

In an application to the spine, arthrodesis is used to block two vertebrae relative to each other. Stabilization is generally obtained by fusion of the two vertebrae, which requires them previously to be held stationary to each other by means of vertebral implants.

Basically, a vertebra comprises, at the front, a vertebral body having a posterior portion from which there extend two pedicles, each connected to the spinous process by a lamina. The pedicles and the lamina define a canal in which the spinal cord or the nerve roots of the cauda equina extend. From the pedicles there extend articular facets for co-operating with the facets of adjacent vertebrae in order to guide the vertebrae relative to one another during their relative movement.

Several types of implant exist for performing arthrodesis.

By way of example, it is known to connect two vertebrae together by using rods fastened to each vertebra by pedicle screws, i.e. screws that are dimensioned to be engaged in the pedicles of vertebrae. Since the pedicles are close to the nerves running along the spine, correct placement of pedicle screws is tricky and improper positioning can be a source of complications.

In another arthrodesis method, use is made of transfacet screws engaged in the facets using the Boucher technique. However, while they are being put into place, those transfacet screws may be difficult to position and their anchoring in the superior facet may be defective (inadequate bone retention).

In order to improve bone retention, another "translaminar facet" technique has been developed by Magerl. That technique has the advantage of improving anchoring of the screws. However, the advantage that is required is complex to implement.

OBJECT OF THE INVENTION

An object of the invention is to provide means that facilitate putting a vertebral implant into place and that include transfacet screws.

SUMMARY OF THE INVENTION

To this end, the invention provides a vertebral implant comprising a first body and a second body that are hinged to each other, and two transfacet connection screws, each having a threaded shank provided with a partially spherical head. Each body comprises both a portion for connection to the other body and also a base having a soleplate arranged to face a portion of vertebra that has been exposed by laminectomy. The base is provided with a hole having a first end opening out into the soleplate and a second end that opens out at the opposite end and that is provided with a recess for receiving the screw head, and the base is also provided with a slot extending along the hole and opening out laterally into the hole in order to enable lateral insertion of the screw in the hole.

The transfacet connection screws are dimensioned to pass through a portion of a first vertebra and to be housed in the facet of a second vertebra, adjacent to the first, and to which it is sought to fasten the first vertebra. The portion via which each transfacet screw penetrates has been exposed by laminectomy, which facilitates putting the screws into place. The bodies of the implant are put into place after inserting the screws, which is more comfortable for the practitioner. The bodies of the implant ensure that the screws are connected together mechanically and they reinforce the vertebra while at the same time also protecting nerve structures.

The invention also provides an instrument for putting screws into place in a vertebra after laminectomy, the instrument comprising forceps having a first jaw co-operating with a guide tube and a second jaw. The guide tube has an open first end arranged to bear on a portion of vertebra left uncovered by the laminectomy and an open second end arranged to enable a drilling member to be inserted in the guide tube. The second jaw has an end extending substantially facing the first end of the guide tube.

This instrument makes it possible to perform drilling in accurate, reliable, and repeatable manner. In particular, the fact that the second jaw has its free end in the vicinity of the axis of the guide tube and therefore of the drill bit makes it possible for the practitioner to visualize the final position of the hole that is to be made.

Finally, the invention provides a method of putting at least one implant into place on at least a first vertebra and a second vertebra of a patient, the second vertebra extending immediately underneath the first vertebra, the implant comprising transfacet screws. The method comprises the steps of:

performing laminectomy in order to uncover two portions of the first vertebra;

engaging the transfacet screws, along a translaminar aiming line, in each of the uncovered portions by passing through the bottom facet of the first vertebra until it penetrates the top facet of the second vertebra in such a manner that each screw secures the bottom facet of the first vertebra and the top facet of the second vertebra.

The aiming line is preferably of the Magerl type and is oriented so as to ensure drilling of both facing facets without interfering with the spinous process of the vertebra located below.

Other characteristics and advantages of the invention appear on reading the following description of particular non-limiting embodiments of the invention.

BRIEF DESCRIPTION OF THE FIGURES

Reference is made to the accompanying drawings, in which.

DETAILED DESCRIPTION OF THE INVENTION

Figure 1:
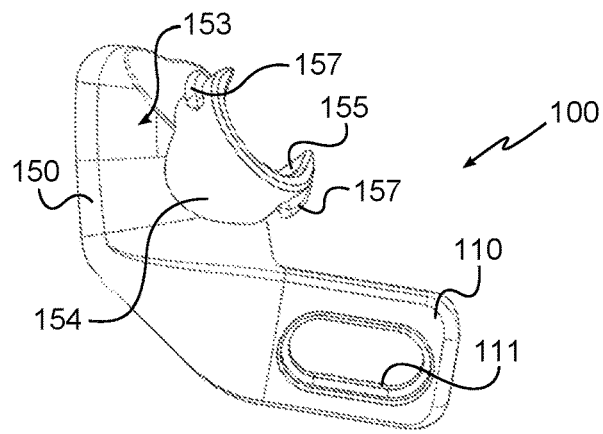
FIG. 1 is a front view of the first body of the implant.
Figure 2:
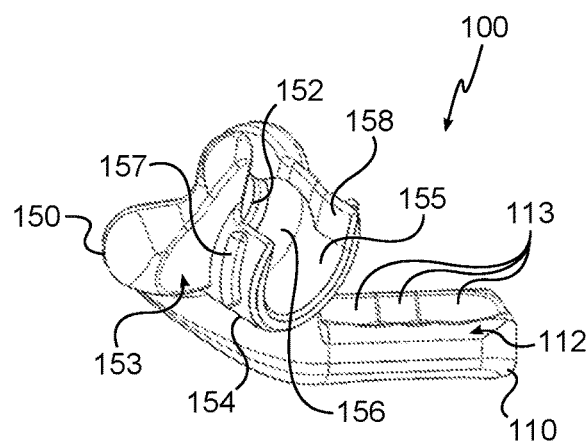
FIG. 2 is a view from above of the first body of the implant.
Figure 3:
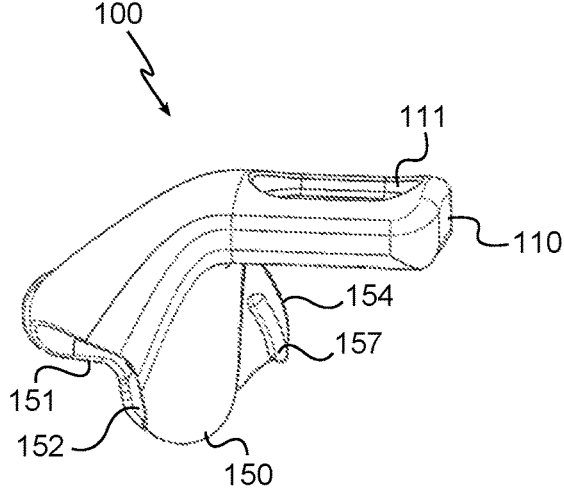
FIG. 3 is a view from below of the first body of the implant.
Figure 4:
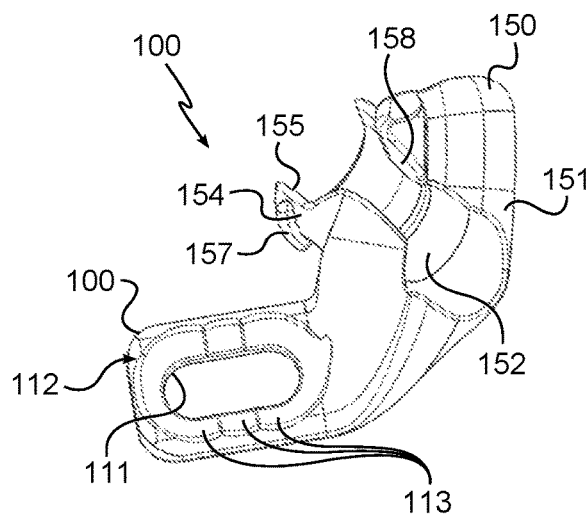
FIG. 4 is a view from behind of the first body of the implant.
Figure 5:
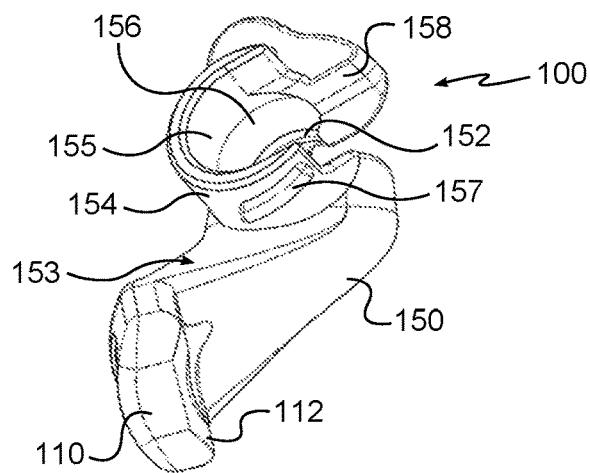
FIG. 5 is a side view of the first body of the implant.

With reference to FIGS. 1 to 15, the vertebral implant of the invention comprises a first body generally given the reference 100, a second body generally given the reference 200, and two screws, given the reference 1.

Each screw 1 comprises a threaded shank 2 provided with a head 3 having an outside surface 4 that is substantially spherical and provided with a socket 5, in this example a hexagonal socket, in order to co-operate with a screw-driver tool. The screws 1 are dimensioned to provide a transfacet connection.

Figure 8:
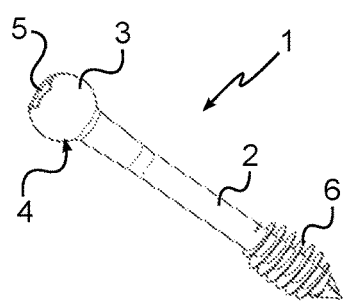
FIG. 8 is a view of a screw of the implant in a first embodiment.

In the first embodiment of the screw, shown in FIG. 8, the threaded shank comprises a single threaded segment 6 situated close to the free end of the threaded shank 2. The threaded segment 6 has an outside diameter that is greater than the diameter of the rest of the threaded shank 2 between the threaded segment 6 and the head 2.

Figure 9:
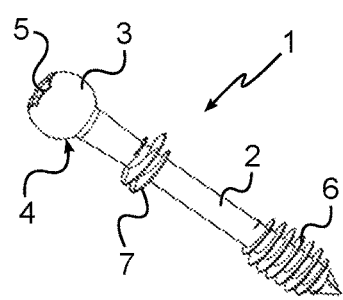
FIG. 9 is a view of a screw of the implant in a second embodiment.
Figure 10:
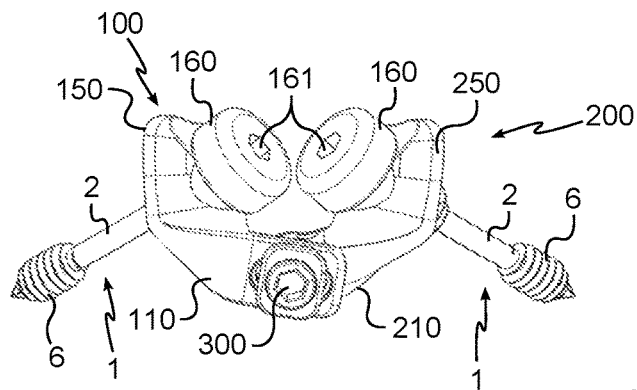
FIG. 10 is a front view of the assembled implant.
Figure 11:
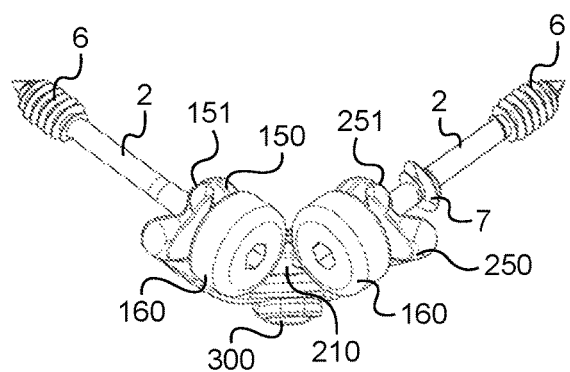
FIG. 11 is a view from above of the assembled implant.
Figure 12:
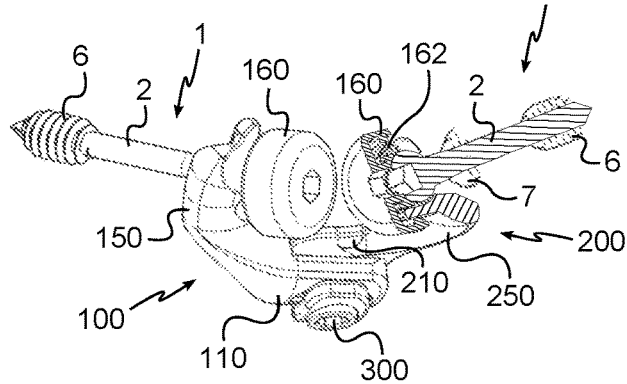
FIG. 12 is a view from above of the assembled implant, partially in section on a plane containing the central axis of one of the screws.
Figure 13:
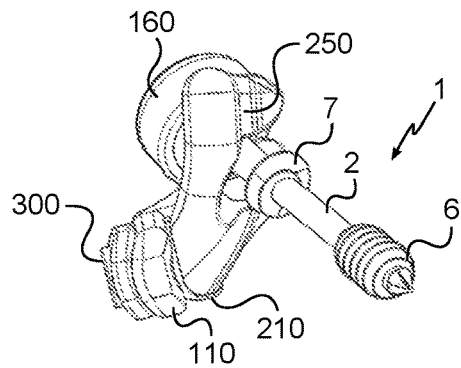
FIG. 13 is a side view of the assembled implant.
Figure 14:
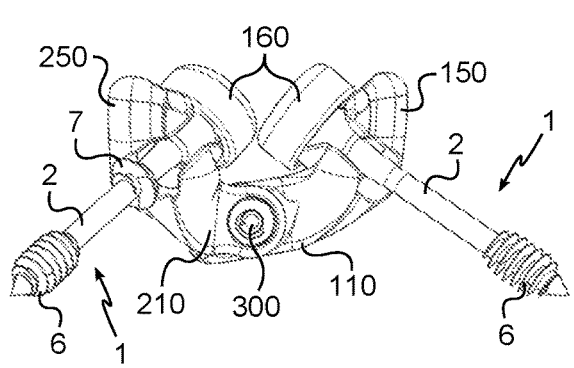
FIG. 14 is a view from behind of the assembled implant.
Figure 15:
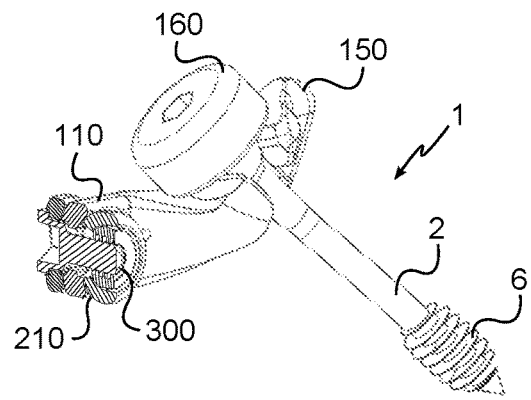
FIG. 15 is a perspective view of the assembled implant, with a section along a midplane containing the axis of the connection bolt.
Figure 16:
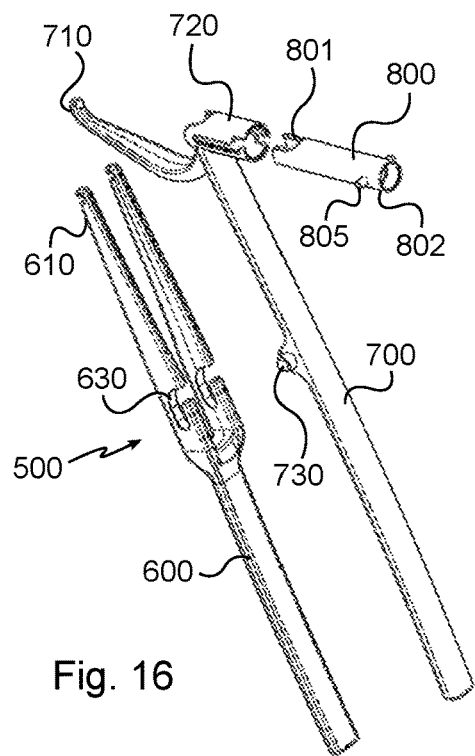
FIG. 16 is an exploded perspective view of the instrument for putting the screws of the implant into place.
Figure 17:
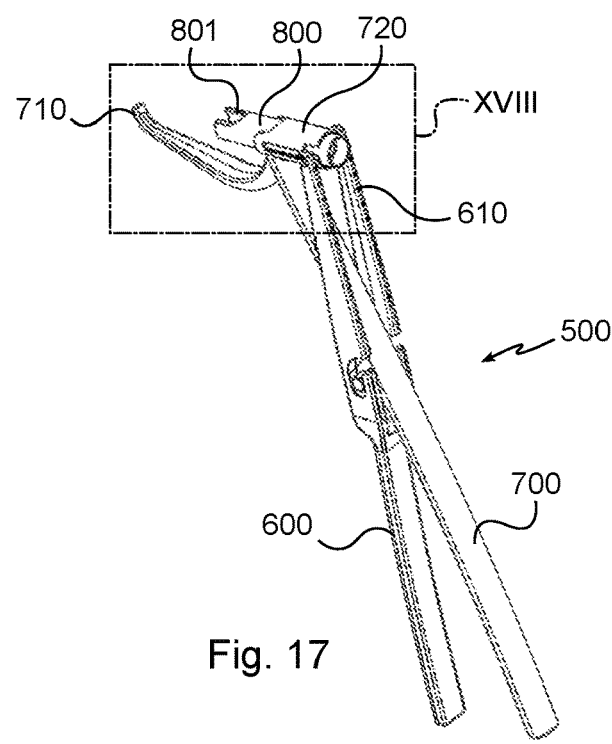
FIG. 17 is a perspective view of the instrument.
Figure 18:
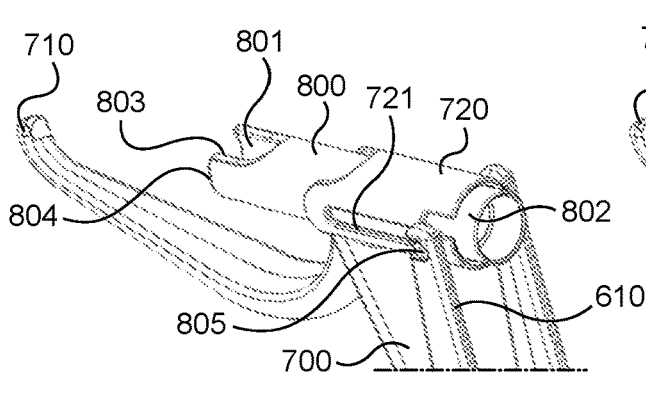
FIG. 18 is a larger-scale detail view of the zone XVIII of FIG. 17, the instrument being in its open state.
Figure 19:
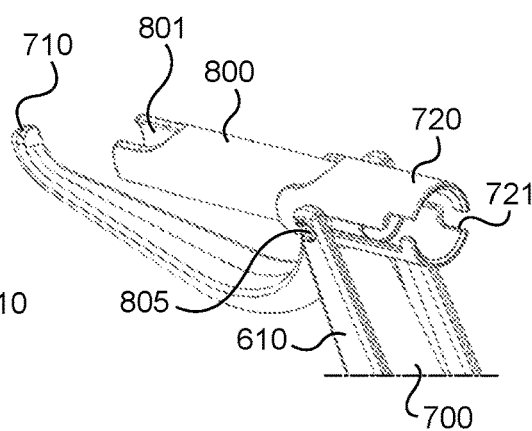
FIG. 19 is view analogous to that shown in FIG. 18 of the instrument in its closed state.

In the second embodiment of the screw, shown in FIG. 9, the threaded shank 2 of the screw 1 comprises two threaded segments that are spaced apart: one, referenced 7, situated close to the head 3 of the screw 1 and the other, referenced 6, situated close to the free end of the threaded shank 2. The threaded segments 6, 7 have an outside diameter that is greater than the diameter of the non-threaded segment extending between the threaded segment 7 and the head 3 and greater than the diameter of the non-threaded segment extending between the threaded segments 6, 7. The threaded segment 7 has a pitch greater than the pitch of the threaded segment 6. The threaded segment 7 has a diameter that is greater than the diameter of the threaded segment 6. This makes it possible to press together the bone portions in which the screw is engaged.

The first body 100 comprises a portion 110 for connection to the body 200 and a base 150 (see FIGS. 1 to 5 in particular).

The base 150 comprises a soleplate 151 arranged to face a portion of vertebra that has been exposed by laminectomy. The base 150 is provided with a hole 152 for receiving the non-threaded segment of the shank 2 extending in the vicinity of the head 3 of the screw 1. The hole 152 has a first end that opens out into the soleplate 151 and a second end that opens out at the opposite end in a surface 153 of the base 150. A collar 154, of tubular shape, projects from the surface 153 around the outlet of the second end of the hole 152 in order to define a recess 155 that is in communication with the hole 152 and has a diameter that is sufficient for receiving the head 3 of the screw 1. The recess 155 has an end wall 156 of shape that is substantially frustoconical and designed to come into contact with the outside surface 4 of the head 3 by providing a ball-joint connection (in a variant, the end wall 156 may be a portion of a sphere). The collar 154 is provided externally with a thread 157 for co-operating by screw-fastening with a cover 160 comprising an end wall surrounded by a tapped annular rim. The rim of the cover 160 is provided externally with a socket 161 that is identical to the socket 5 in order to be able to co-operate with the same screw-driver tool. The end wall of the cover 160 is provided internally with a block 162 that projects towards the inside of the cover 160 and that has a concave free surface in the form of a spherical cap of transverse dimension that is greater than that of the socket 5 in such a manner that, when the cover 160 is tightened on the collar 154, the block 162 bears against the outside surface 4 of the head 3 and presses the head against the frustoconical surface 156 that forms a shoulder of the base 150. The head 3 is therefore clamped between the frustoconical surface 156 and the block 162.

The base 150 is also provided with a slot 158 extending along the hole 152 and along the recess 155 and opening out laterally into the hole 152 and the recess 155 in order to enable the non-threaded segment of the shank 2 to be inserted laterally into the hole 152 and the head 3 to be inserted laterally into the recess 155.

The connection portion 110 projects laterally from the base 150 and includes an oblong through opening 111 for passing a bolt 300. The oblong opening 111 has a major axis parallel to the lateral direction. The connection portion 110 has a concave rear surface 112 that is curved around the lateral direction and that includes hemispherical setbacks 113 distributed along the major axis of the oblong opening 111.

Figure 6:
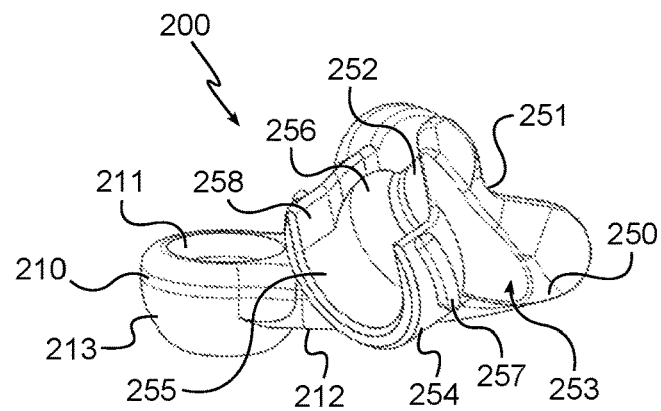
FIG. 6 is a view from above of the second body of the implant.
Figure 7:
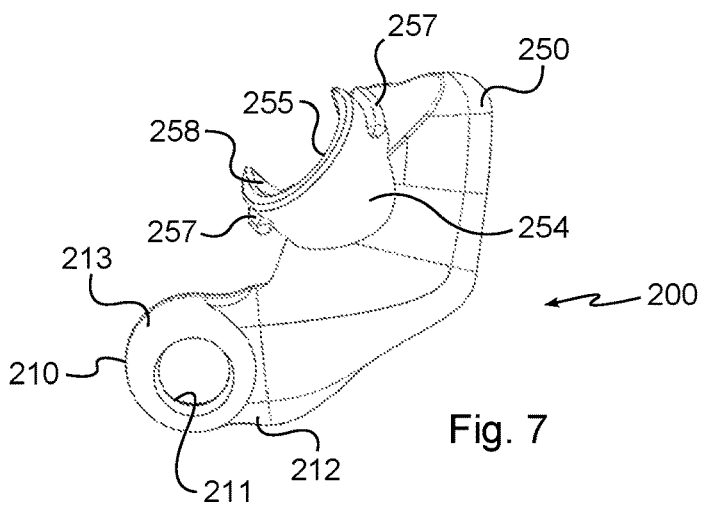
FIG. 7 is a front view of the second body of the implant.

The second body 200 comprises both a portion 210 for connection to the body 100 and also a base 250 (see FIGS. 6 and 7 in particular).

The base 250 comprises a soleplate 251 arranged to face a portion of vertebra that has been exposed by laminectomy. The base 250 is provided with a hole 252 for receiving the non-threaded segment of the shank 2 extending in the vicinity of the head 3 of the screw 1. The hole 252 has a first end that opens out into the soleplate 251 and a second end that opens out at the opposite end in a surface 253 of the base 250. A collar 254, of tubular shape, projects from the surface 253 around the outlet of the second end of the hole 252 in order to define a recess 255 that is in communication with the hole 252 and has a diameter that is sufficient for receiving the head 3 of the screw 1. The recess 255 has an end wall 256 of shape that is substantially frustoconical and designed to come into contact with the outside surface 4 of the head 3 by providing a ball-joint connection. The collar 254 is provided externally with a thread 257 for co-operating by screw-fastening with a cover 160 comprising an end wall surrounded by a tapped annular rim. The rim of the cover 160 is provided externally with a socket 161 that is identical to the socket 5 in order to be able to co-operate with the same screw-driver tool. The end wall of the cover 160 is provided internally with a block 162 that projects towards the inside of the cover 160 and that has a concave free surface in the form of a spherical cap of transverse dimension that is greater than that of the socket 5 in such a manner that, when the cover 160 is tightened on the collar 254, the block 162 bears against the outside surface 4 of the head 3 and presses the head against the frustoconical surface 256 that forms a shoulder of the base 250. The head 3 is therefore clamped between the frustoconical surface 256 and the block 162.

The base 250 is also provided with a slot 258 extending along the hole 252 and along the recess 255 and opening out laterally into the hole 252 and the recess 255 in order to enable the non-threaded segment of the shank 2 to be inserted laterally into the hole 252 and the head 3 to be inserted laterally into the recess 255.

The connection portion 210 projects laterally from the base 250 and includes a cylindrical through opening 211 for passing a bolt 300. The cylindrical opening 211 has one end that opens out in the center of a cup 213 projecting from a front surface 212 of the connection portion 210.

When the implant is assembled (see FIGS. 10 to 15 in particular). It should be observed that both types of screw are used in the implant for the purposes of illustration. Naturally a single type is preferably used in practice, the cup 213 is received in one of the hemispherical setbacks 113 in such a manner that the connection portions 110, 210 of the bodies 100, 200 are arranged to form between them substantially a ball-joint connection. The plurality of hemispherical setbacks 113 make it possible to adjust the connection portion 210 while it is in position relative to the connection portion 110. The bolt 300 conventionally comprises, a screw, a nut, and a washer bearing against the connection portion 110. The washer has a cylindrical rear surface having a central axis passing substantially through the geometrical center of the cup 213.

With reference to FIGS. 16 to 19, the instrument of the invention is arranged for putting the screw into place in a vertebra after laminectomy.

The instrument comprises forceps 500 having a first lever 600 with a first jaw 610 secured thereto and a second lever 700 with a second jaw 710 secured thereto, that is hinged at its center to the first lever 600.

The first jaw 610 co-operates with a guide tube 800 having a first open end 801 arranged so as to bear on a portion of vertebra left uncovered by the laminectomy and a second open end 802 arranged to enable a drill bit and screws 1 to be inserted into the guide tube 800. The end 801 is provided with two axial notches 803 and has a serrated front surface 804 for biting into the bone. The guide tube 800, is mounted in a housing 720, secured to the second lever 700, to slide along the central axis of the guide tube 800 and the first lever 600 is hinged to the guide tube 800 in such a manner that moving the levers 600, 700 closer together causes the guide tube 800 to slide in the direction of the second jaw 710. The guide tube 800 is provided externally with two symmetrical lugs 805 engaged in grooves 721 of the housing 720 in order to form a bayonet type connection. The first jaw 610 comprises two arms, each provided with a notch pivotally receiving one of the lugs 805 in such a manner as to be able to push the guide tube 800 during closing of the forceps 500.

Figure 23:
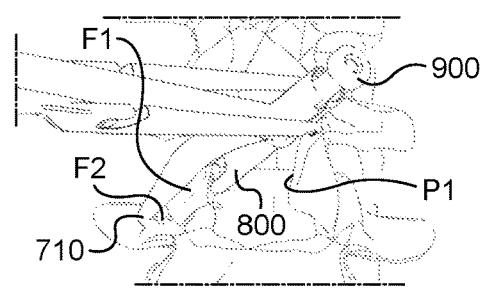
Figure 24:
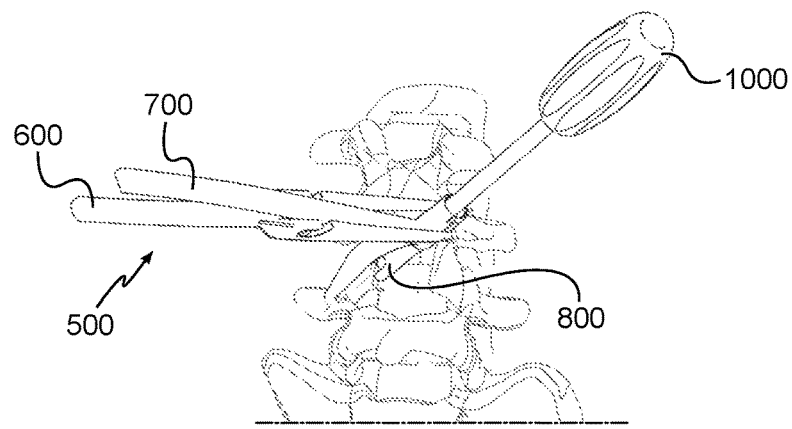

The guide tube 800 has a diameter that is large enough to receive a drill bushing 900 (see FIG. 23) in removable manner and, once the drill bushing 900 is removed, for passing one of the screws 1 and of a screwdriver 1000 (see FIG. 24) that is adapted for turning the screw 1.

The second jaw 710 has an end that coincides substantially with the central axis of the guide tube 800. In a variant, the second jaw 710 may be offset relative to the central axis, the major concern being that it is situated substantially facing the front surface 804 in order to enable bone portions to be pinched together (the second jaw 710 may therefore also be slightly offset relative to the front surface 804).

The levers 600, 700 are hinged to each other by interaction between elements of complementary shapes, in this embodiment, lugs 730 that are secured to the second lever 700 and that are engaged in the grooves 630 of the first lever 600.

It should be observed that the levers 600, 700 are easily separable from each other, in the same way as the first lever 600 is separable from the guide tube 800 and the guide tube 800 is separable from the housing 720. This makes it easier to dismantle and thus clean and sterilize the instrument.

The method of putting an implant into place on at least a first vertebra and a second vertebra of a patient is described below with reference to FIGS. 20 to 29.

Figure 20:
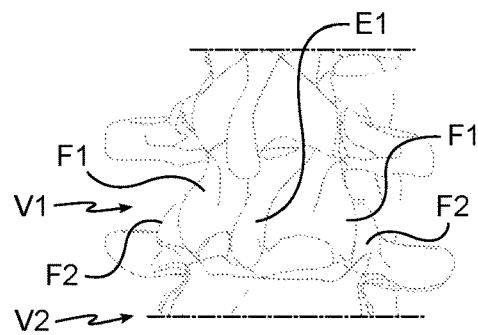
FIGS. 20 to 29 are perspective views showing the implant being put into place in the lumbar region of a spine.

The lumbar region of the spine of the patient before surgery is shown in FIG. 20.

It shows the first vertebra V1 and the top portion of the second vertebra V2 that extends immediately underneath the first vertebra V1, the inferior facets F1 of the vertebra V1, the superior facets F2 of the vertebra V2 and the spinous process E1 of the vertebra V1.

Figure 21:
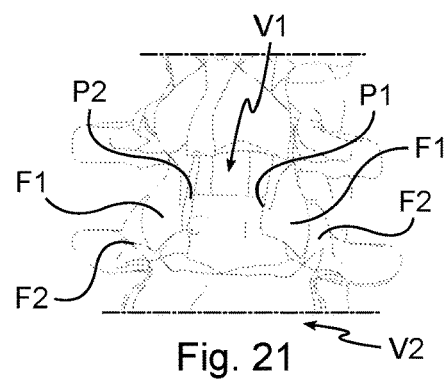
Figure 22:
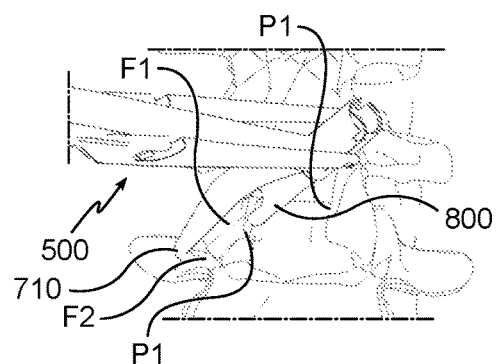

The method begins by performing laminectomy in order to uncover substantially symmetrically both portions P1 of the first vertebra (FIG. 21).

The instrument is then put into place in order to define the aiming line along which the first hole will extend and therefore, at a later stage, along which one of the screws 1 will extend (in this embodiment the screw is on the left, when the spine is considered in the vertical position), which screw will also fasten the body 100 of the implant.

It should be observed that the end of the jaw 710 comes into position behind the facet F2 while the front surface 804 of the guide tube 800 bears against the portion left uncovered on the left by the laminectomy. The guide tube 800 and the housing 720 pass under the spinous process of the vertebra situated above the vertebra V1.

The aiming line is translaminar (but the middle portion of the lamina has been removed) and of the Magerl type.

The drill bushing 900 is put into place in the guide tube 800 and a drill bit is inserted therein. A hole is thus made along the aiming line and passes through the inferior facet F1 of the first vertebra V1 until it penetrates the superior facet F2 of the second vertebra V2.

The drill bushing is removed and a screw 1 is inserted in the guide tube 800 with the end of the screwdriver 1000 in order to tighten the screw 1 in the hole made in the facets F1, F2.

The screwdriver and the instrument may then be removed.

Figure 25:
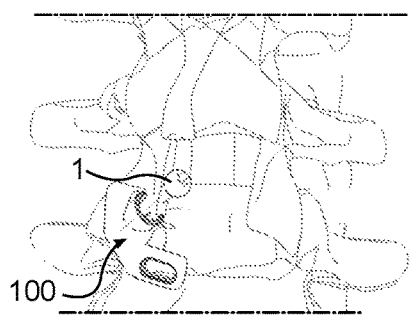
Figure 26:
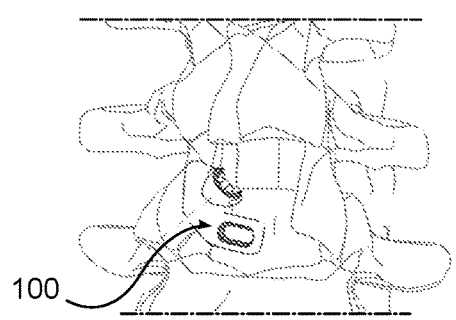

The screw is not screwed-in fully so that the body of the implant can be engaged laterally on the portion of the screw (the head segment) that projects from the portion of vertebra left uncovered by the laminectomy (FIG. 25). After engagement of the implant body, tightening of the screw 1 is completed (FIG. 26).

Figure 27:
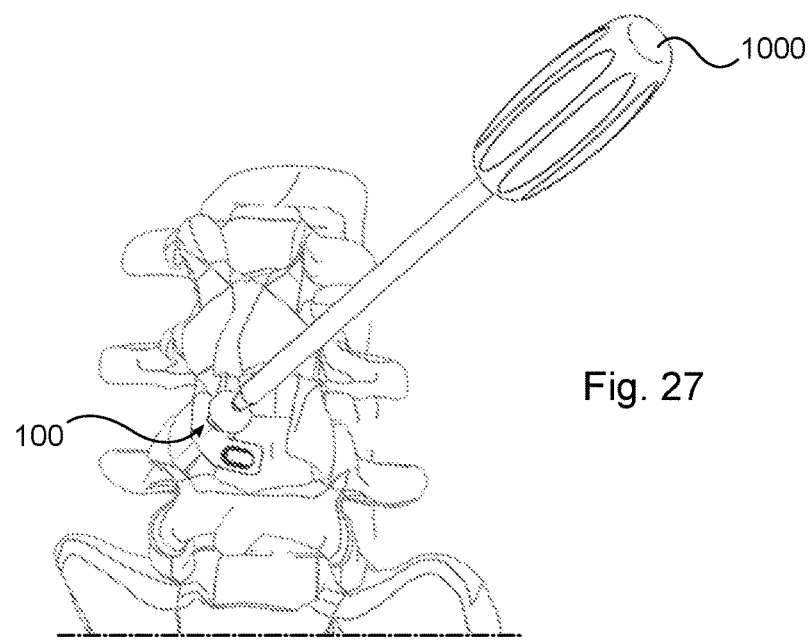
Figure 28:
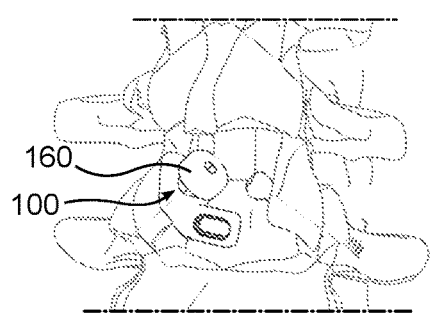

The cover 160 is then put into place (FIGS. 27 and 28).

The instrument is positioned on the portion of the vertebra V1 left uncovered on the right by the laminectomy. The same operations as described above are then performed in order to fasten a screw 1 in the facets F1, F2 on the right.

The first body 100 is thus mounted on the left screw 1, the second body 200 on the right screw 1.

The connection portion 210 is brought behind the connection portion 110 and the hemispherical bulge 213 is engaged in one of the setbacks 113, and the bolt 300 is put into place without being tightened.

Figure 29:
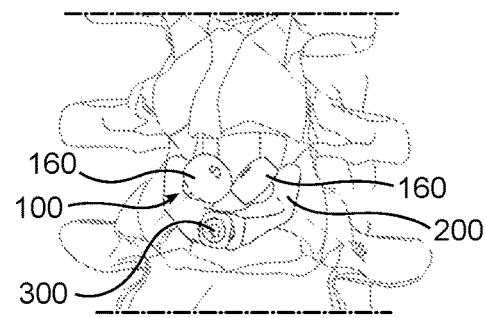

The covers 160 and the bolt 300 are tightened progressively (FIG. 29).

In a variant, for certain pathologies, it is possible to couple one or more implants mounted on adjacent vertebrae.

By way of example, this involves performing laminectomy of the second vertebra V2, and fastening an implant on the second vertebra V2 and the vertebra below it in the same way as on the vertebrae V1 and V2.

The same procedure may be performed on all adjacent vertebrae, and repeated depending on the assembly envisaged by the surgeon.

Figure 30:
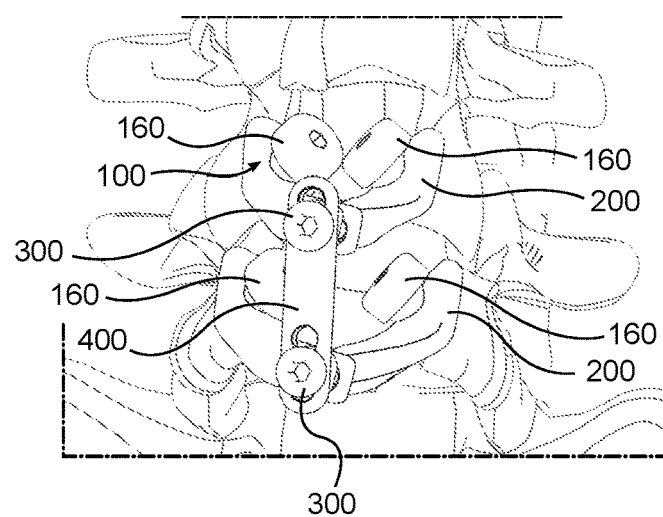
FIG. 30 is a view analogous to that shown in FIG. 29 showing two implants in place in the lumbar region of a spine and coupled together.

The bolts 300 are then used to fasten a bar 400 to two or more implants (FIG. 30). The bar 400 includes a plurality of openings for passing bolts 300 therethrough in such a manner as to enable them to be positioned adjustably. Furthermore, in multi-level assemblies, the bar 400 is shaped by the surgeon so as to match the curvature of the spine fitted with implants.

Naturally, provision should be made for implants and screws of several sizes so as to be able to adapt to different morphologies.

Naturally, the invention is not limited to the embodiments described but encompasses any variant coming within the ambit of the invention as defined by the claims.

In particular, the implant may be of shapes other than those described and shown.

The covers may be fastened in different ways on the base. The rim 154 may be tapped in order to receive a threaded cover. The covers may be fastened other than by screw-fastening and for example they could be fastened by means of a bayonet connection.

The drilling member may be a drill bit for making a hole before each transfacet screw is put into place or it may be the screw itself when the transfacet screw is arranged to be a self-drilling screw.

The invention claimed is:

1. A vertebral implant comprising a first body and a second body that are hinged to each other, each one of the first body and the second body being arranged to be fastened by only one transfacet connection screw, the transfacet connection screws being attachable to opposite sides of a vertebra, each transfacet connection screw having a threaded shank provided with a partially spherical head, each body comprising both a portion for connection to the other body and also a base having a soleplate arranged to face towards a portion of vertebra that has been exposed by laminectomy, the base of each body being provided with a hole having a first end opening out into the soleplate and a second end that opens out at the opposite end and that is provided with a recess for receiving the head of said transfacet connection screw, the base of each body also being provided with a slot extending along the hole and opening out laterally into the hole in order to enable lateral insertion of said transfacet connection screw in the hole and the base of each body cooperating with a cover arranged to tighten the head of the screw against a shoulder of the base;

wherein the base of each body comprises a collar provided with a thread for co-operating by screw-fastening with the cover.

2. The implant according to claim 1, wherein the base of each body cooperates with the cover by screw-fastening.

3. The implant according to claim 2, wherein the second end of the hole is defined by a collar that projects from the body and that is provided externally with a thread in order to cooperate with the cover.

4. The implant according to claim 1, wherein the connection portions of the bodies are arranged to form between them substantially a ball-joint connection and to be connected to each other by a bolt which is arranged not to be in connection with the vertebra.

5. The implant according to claim 4, wherein the connection portion of the first body includes an oblong opening for passing the bolt and the connection portion of the second body includes a cylindrical opening for passing the bolt.

6. The implant according to claim 5, wherein the connection portion of the first body includes, besides the connection portion of the second body, hemispherical setbacks distributed along the oblong hole in order to accommodate in part a spherical cup-shaped portion of the connection portion of the second body.

7. The implant according to claim 1, wherein the threaded shank of each screw comprises two threaded segments that are spaced apart: one situated close to the head of the screw and the other situated close to a free end of the shank.

8. The implant according to claim 7, wherein the threaded segment situated close to the head of the screw has a greater pitch than the pitch of the threaded segment situated close to the free end of the shank.

9. The implant according to claim 7, wherein the threaded segment situated close to the head of the screw has a diameter that is greater than the diameter of the threaded segment situated close to the free end of the shank.

10. The implant according to claim 1, wherein each cover comprises an end wall surrounded by a tapped annular rim.

11. The implant according to claim 10, wherein the end wall of each cover is provided internally with a block that projects towards the inside of the cover and that has a concave free surface in the form of a spherical cap in such a manner that, when the cover is tightened on the collar, the block bears against an outside spherical surface of the head of the screw and presses the head against a frustoconical surface that forms the shoulder of the base.

12. A vertebral implant comprising a first body and a second body that are hinged to each other, each one of the first body and the second body being arranged to be fastened to a vertebra by only one transfacet connection screw, each transfacet connection screw having a threaded shank provided with a partially spherical head, each body comprising both a portion for connection to the other body and also a base having a soleplate arranged to face towards a portion of vertebra that has been exposed by laminectomy, the base of each body being provided with a hole having a first end opening out into the soleplate and a second end that opens out at the opposite end and that is provided with a recess for receiving the head of said transfacet connection screw, the base of each body also being provided with a slot extending along the hole and opening out laterally into the hole in order to enable lateral insertion of said transfacet connection screw in the hole and the base of each body cooperating with a cover arranged to tighten the head of the screw against a shoulder of the base, the body being arranged so that when fastened to the vertebra the first body and the second body being hinged to each other around an axis perpendicular to a front plane of the vertebra;

wherein the base of each body comprises a collar provided with a thread for co-operating by screw-fastening with the cover.

* * * * *